United States Patent [19]

Evers et al.

[11] 4,098,910
[45] Jul. 4, 1978

[54] FLAVORING WITH CERTAIN 3-FURYL ALKYL DISULFIDES

[75] Inventors: William J. Evers, Middletown; Howard H. Heinsohn, Jr., Hazlet; Manfred Hugo Vock, Locust, all of N.J.

[73] Assignee: International Flavors & Fragrances Inc., New York, N.Y.

[21] Appl. No.: 551,045

[22] Filed: Feb. 19, 1975

[51] Int. Cl.² ............................................. A23L 1/231
[52] U.S. Cl. .................................................... 426/535
[58] Field of Search ....................................... 426/535

[56] References Cited

U.S. PATENT DOCUMENTS 3,666,495  5/1972  Evers .................................... 426/535

*Primary Examiner*—Joseph M. Golian

*Attorney, Agent, or Firm*—Arthur L. Liberman; Franklin D. Wolffe

[57] ABSTRACT

Novel 3-furyl alkyl disulfides having the formula:

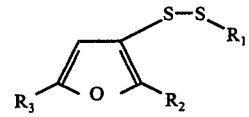

wherein $R_1$ is $C_1$-$C_7$ lower alkyl or $C_5$-$C_6$ cycloalkyl; $R_2$ and $R_3$ are each selected from the group consisting of hydrogen and methyl, at least one of $R_2$ or $R_3$ being methyl provided that when $R_1$ is methy, each of $R_2$ and $R_3$ is methyl, such 3-furyl alkyl disulfides being useful in altering the organoleptic properties of foodstuffs.

2 Claims, No Drawings

FLAVORING WITH CERTAIN 3-FURYL ALKYL DISULFIDES

BACKGROUND OF THE INVENTION

The present invention relates to novel 3-furyl alkyl disulfides.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is noteable in products having meaty and roasted flavor characteristics.

Reproduction of sweet meat, roasted meat, liver flavors and aromas and hydrolyzed vegetable protein like flavors and aromas has been the subject of the long and continuing search by those engaged in the production of foodstuffs, e.g., luncheon meats such as liverwurst sausages. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted meat products (e.g., "roast-beef-like") and liver products are required.

Moreover, there are a great many meat containing or meat based foods presently distributed in a preserved form. Examples being condensed soups, dry-soup mixes, dry meat, freeze-dried or lyophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have sweet meat, roasted meat and/or liver taste and aroma nuances.

U.S. Pat. No. 3,666,495 has to do with certain furan derivatives having desirable meat, roast meat and roasted fragrance and flavor notes. Among the furan derivatives disclosed in said patent are methyl-(2-methyl-3-furyl) trisulfide obtained by the reaction of 2-methyl-3-furan thiol with methyl disulfur chloride at a temperature of from −60° C to 0° C, and methyl-(2-methyl-3-furyl) disulfide obtained by reacting 2-methyl-3-furan thiol with methane sulfenyl chloride.

None of the 3-furyl alkyl disulfides of the instant invention is disclosed in U.S. Pat. No. 3,665,495.

THE INVENTION

The present invention provides novel 3-furyl alkyl disulfides for altering the organoleptic properties of foodstuffs. Briefly, the novel compounds are 3-furyl alkyl disulfides having the formula:

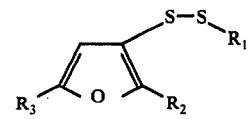

wherein $R_1$ is $C_1$–$C_7$ lower alkyl or $C_5$–$C_6$ cycloalkyl; $R_2$ and $R_3$ are each selected from the group consisting of hydrogen and methyl, at least one of $R_2$ or $R_3$ being methyl provided that when $R_1$ is methyl, each of $R_2$ and $R_3$ is methyl.

Thus, 3-furyl alkyl disulfides contemplated within the scope of our invention are:

| 3-Furyl Alkyl Disulfide Compounds | Structure |
| --- | --- |
| methyl(2,5-dimethyl-3-furyl) disulfide | 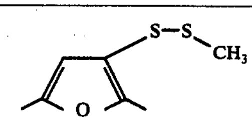 |
| ethyl(2-methyl-3-furyl) disulfide | 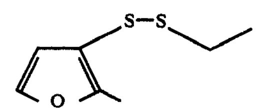 |
| ethyl(2,5-dimethyl-3-furyl) disulfide | 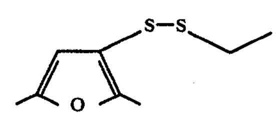 |
| n-propyl(2-methyl-3-furyl) disulfide | 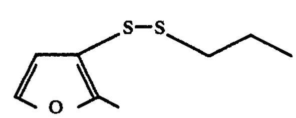 |
| n-propyl(2,5-dimethyl-3-furyl) disulfide | 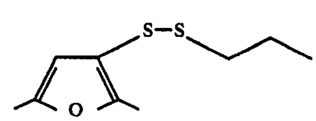 |
| isoamyl(2-methyl-3-furyl) disulfide | 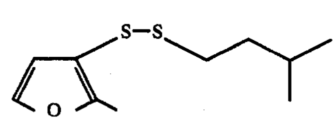 |
| cyclohexyl(2-methyl-3-furyl) disulfide | 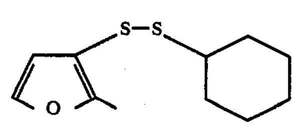 |
| isoamyl(2,5-dimethyl-3-furyl) disulfide | 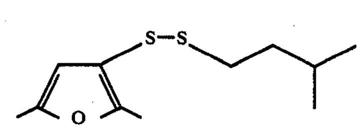 |

| 3-Furyl Alkyl Disulfide Compounds | Structure |
|---|---|
| n-heptyl(2-methyl-3-furyl) disulfide | 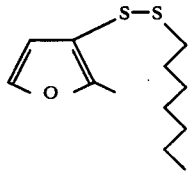 |

A number of the novel disulfide compounds of our invention may be produced according to processes which comprise the steps of:

(i) Carrying out a reaction by intimately admixing a lower alkyl disulfide having the formula:

$$R_1-S-S-R_1$$

with a 3-furan thiol having the formula:

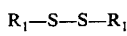

in the presence of an alkali metal or base such as an alkali metal lower alkoxide at a temperature in the range of from about 15° up to about 150° C to form a reaction mass; and (ii) Physically separating said alkyl furyl disulfide from said reaction mass;
wherein $R_1$ is selected from the group consisting of ethyl, n-propyl, i-propyl and each of $R_2$ and $R_3$ is selected from the group consisting of hydrogen and methyl, at least one of $R_2$ or $R_3$ being methyl with the proviso that when $R_1$ is methyl, each of $R_2$ and $R_3$ is methyl; in order to provide an alkyl furyl disulfide compound having the structure:

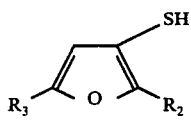

The following table sets forth examples of specific reactants and the resulting products produced using the process of our invention:

| Lower Alkyl Disulfide Reactant | 3-Furan Thiol Reactant | 3-Furyl Alkyl Disulfide Product |
|---|---|---|
| Dimethyl disulfide | 5-methyl-3-furan thiol | methyl(5-methyl-3-furyl) disulfide |
| Dimethyl disulfide | 2,5-dimethyl-3-furan thiol | methyl(2,5-dimethyl-3-furyl) disulfide |
| Diethyl disulfide | 2-methyl-3-furan thiol | ethyl(2-methyl-3-furyl) disulfide |
| Diethyl disulfide | 5-methyl-3-furan thiol | ethyl(5-methyl-3-furyl) disulfide |
| Diethyl disulfide | 2,5-dimethyl-3-furan thiol | ethyl(2,5-dimethyl-3-furyl) disulfide |
| Di-n-propyl disulfide | 2-methyl-3-furan thiol | n-propyl(2-methyl-3-furyl) disulfide |
| Di-n-propyl disulfide | 5-methyl-3-furan thiol | n-propyl(5-methyl-3-furyl) disulfide |
| Di-n-propyl disulfide | 2,5-dimethyl-3-furan thiol | n-propyl(2,5-dimethyl-3-furyl disulfide |
| Di-i-propyl disulfide | 2-methyl-3-furan thiol | i-propyl(2-methyl-3-furyl) disulfide |
| Di-i-propyl disulfide | 5-methyl-3-furan thiol | i-propyl(5-methyl-3-furyl) disulfide |
| Di-i-propyl disulfide | 2,5-dimethyl-3-furan thiol | i-propyl(2,5-dimethyl-3-furyl) disulfide |

Although the reaction will proceed in the presence of an alkali metal such as sodium, potassium or lithium, or a base such as any alkali metal lower alkoxide, the following alkali metal lower alkoxides are preferred:
Sodium methoxide;
Sodium ethoxide;
Sodium-n-propoxide;
Potassium methoxide;
Potassium ethoxide;
Potassium isopropoxide;
Potassium-t-butoxide;
Lithium methoxide; and
Lithium ethoxide
with sodium methoxide being most preferential due to its relatively low cost.

The mole ratio of alkali metal or base to methyl-3-furan thiol reactant may vary from 0.005:1 up to 0.1:1 with a range of from 0.01:1 up to 0.03:1 being preferred.

The mole ratio of dialkyl disulfide to methyl-3-furan thiol in the reaction mass may vary from 1:1 up to 10:1 with the dialkyl disulfide being the material in excess and with a mole ratio of dialkyl disulfide ot methyl-3-furan thiol of approximately 5:1 being preferred.

The reaction temperature may vary from 15° up to 150° C with the preferred temperature being a function of:

(1) Time of contact of reactants, high temperatures giving rise to lower reactant contact times; and (2) Desired alkyl ($R_1$) substituent in the compound having the structure:

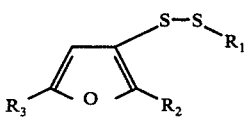

With time of reaction remaining constant, higher temperatures of reaction are required, the greater the molecular weight of the $R_1$ substituent. Thus, for example, the following table shows the preferred reaction temperature, given specific $R_1$ substituents:

| $R_1$ Substituent | Preferred Reaction Temperature Range |
|---|---|
| Methyl | 20–30° C |
| Ethyl | 45–55° C |
| n-Propyl | 75–85° C |

The reaction is preferably carried out at atmospheric pressure; however, pressures greater than atmospheric, e.g., 5 atmospheres may be used.

At the end of the reaction, the reaction product is diluted with hexane or pentane, washed with water, dried, concentrated and distilled, preferably by means of vacuum distillation.

Another process for preparing the 3-furyl alkyl disulfides of our invention which process if particularly preferred when $R_1$ is alkyl of from five up to seven carbon atoms or cycloalkyl such as cyclopentyl or cyclohexyl involves reacting a 2-alkyl-3-furan thiol with an alkyl or cycloakyl thiol and iodine in the presence of non-reactive solvent, e.g., diethyl ether. Thus, for example, (i) 1-mercapto-3-methyl butane is reacted with iodine (as the oxidizing agent) and 2,5-dimethyl-3-furan thiol, thereby forming isoamyl (2,5-dimethyl-3-furyl) disulfide; and (ii) cyclohexylmercaptan is reacted with iodine and 2-methyl-3-furan thiol to form cyclohexyl(2-methyl-3-furyl) disulfide. This reaction takes place in the presence of a base, e.g., an alkali metal carbonate such as sodium carbonate. The mole ratio of $I_2$:base:2-alkyl-3-furan thiol:alkyl mercaptan is preferably about 0.75:0.75:0.50:1.0. The reaction may be carried out at temperatures in the range of 10° up to 35° C with room temperature being most convenient.

A still further method for preparing the 3-furyl alkyl disulfides of our invention; particularly and preferably desirable where the alkyl substituents contains three or more carbon atoms, involves reaction of a 2-alkyl-3-furan thiol with an approximately equimolar amount of an alkyl sulfenyl chloride. Preferably the alkyl sulfenyl chloride is previously formed in situ by reaction of sulfuryl chloride and a corresponding dialkyl disulfide. This reaction sequence is illustrated by the following equation:

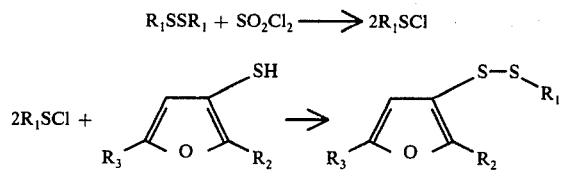

Thus, a thiol such as 2-methyl-3-furanthiol can be reacted with an equimolar amount of n-pentanesulfenyl chloride, $C_5H_{11}SCl$, to produce n-pentyl (2-methyl-3-furyl) disulfide. This reaction also can be carried out in a solvent such as diethyl ether, cyclohexane, hexane, carbon tetrachloride, benzene and the like. The reaction temperature is preferably from −60° up to 0° C at atmospheric pressure.

The following compounds of our invention produced using the above processes have useful organoleptic properties giving rise to their use as foodstuff flavors as set forth in an illustrative manner in the following table:

TABLE I

| 3-Furyl Alkyl Disulfide Compounds | Structure | Flavor Properties |
|---|---|---|
| methyl(2,5-dimethyl-3-furyl) disulfide | [structure: 2,5-dimethyl-3-furyl-S-S-CH₃] | Sweet, roasted meat aroma and sweet, roasted meat flavor with bloody and metallic nuances. |
| ethyl(2-methyl-3-furyl) disulfide | [structure: 2-methyl-3-furyl-S-S-ethyl] | Sweet, roasted, liver-like aroma and sweet, pot roast beef flavor with nutty, liver, bloody and metallic nuances. |
| ethyl(2,5-dimethyl-3-furyl) disulfide | [structure: 2,5-dimethyl-3-furyl-S-S-ethyl] | Sweet, roasted aroma and a sweet, roasted coffee-like flavor. |
| n-propyl(2-methyl-3-furyl) disulfide | [structure: 2-methyl-3-furyl-S-S-n-propyl] | Sweet, roasted meat, meaty aroma and a roast beef, roasted nut flavor with coffee, liver, bloody and metallic nuances. |
| n-propyl(2,5-dimethyl-3-furyl) disulfide | [structure: 2,5-dimethyl-3-furyl-S-S-n-propyl] | Sweet, roasted, meat aroma with a hydrolyzed vegetable protein-like nuance and a roasted meat, sweet, hydrolyzed vegetable protein flavor with metallic and astringent nuances. |
| isoamyl(2-methyl-3-furyl) disulfide | [structure: 2-methyl-3-furyl-S-S-isoamyl] | Meaty-liver, chicken fat, roasted, aroma with metallic, rubbery, sweet and nutty nuances and a meaty, rubbery, roasted flavor with sweet and "baked goods" notes. |
| cyclohexyl(2-methyl-3-furyl) disulfide | [structure: 2-methyl-3-furyl-S-S-cyclohexyl] | Meaty, liver and sweet aroma with a rubbery nuance and a sweet, liver, meaty flavor with rubbery and nutty nuances. |
| isoamyl(2,5-dimethyl-3-furyl) disulfide | [structure: 2,5-dimethyl-3-furyl-S-S-isoamyl] | Sulfury, rubber, liver aroma and sweet, rubbery, sulfury flavor with skunky, liver and bitter nuances. |

TABLE I-continued

| 3-Furyl Alkyl Disulfide Compounds | Structure | Flavor Properties |
|---|---|---|
| n-heptyl(2-methyl-3-furyl) disulfide | 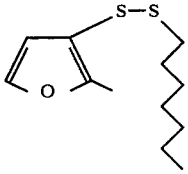 | Sulfury, roasted, meaty flavor and aroma with roast beefy aroma and flavor nuances. |

Each of the 3-furyl alkyl disulfides of our invention has an unexpectedly advantageous, individual impression of flavor (e.g., taste and aroma) properties as indicated in the foregoing table.

The subgenus of 3-furyl alkyl disulfides having the formula:

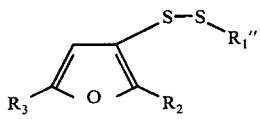

wherein $R_1''$ is $C_5$–$C_6$ alkyl or $C_5$–$C_6$ cycloalkyl, $R_2$ is methyl and $R_3$ is methyl or hydrogen, are particularly preferred for their sweet, liver-meat tastes and aromas.

Furthermore, the sweet/meat taste and aroma of all of the 3-furyl alkyl disulfides of our invention are different from the organoleptic impression of the methyl(2-methyl-3-furyl) disulfide. The organoleptic impression of methyl (2-methyl-3-furyl) disulfide is as follows:

"A corn, meat, hydrolyzed vegetable protein aroma with pot roast nuances; and a corn, pot roast, hydrolyzed vegetable protein flavor with meat, sweet, bloody, coffee, pecan and bread nuances".

Whereas said methyl(2-methyl-3-furyl) disulfide has sweet/meat nuances as secondary notes, in the compounds of our invention, the sweet/meat nuances are the primary notes; and such organoleptic difference is advantageous (for example in the processed meat and sausage industry) and, such a difference is unexpected.

The 3-furyl alkyl disulfides according to the present invention can be used to alter, vary, fortify, modify, enhance or otherwise improve the organoleptic properties, including flavor and/or aroma, of a wide variety of materials which are ingested, consumed, or otherwise organoleptically sensed. The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such 3-furyl alkyl disulfides of this invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma to a consumable article.

The term "foodstuff" as used herein includes both solid and liquid ingestible materials for man or animals, which materials usually do, but need not, have nutritional value. Thus, foodstuffs includes meats, gravies, soups and convenience foods, vegetables, snack foods, dog and cat foods, other veterinary products, and the like.

When the 3-furyl alkyl disulfides according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional material can be used and broadly include other flavor materials, vehicles, stabilizers, thickeners, surface active agents, conditioners, and flavor intensifiers.

Examples of preferred co-flavoring adjuvants are:
Methyl thiazole alcohol (4-methyl-5-betahydroxyethyl thiazole);
2-Methyl butanethiol;
4-Mercapto-2-butanone;
3-Mercapto-4-pentanone;
1-Mercapto-2-propanone;
Benzaldehyde;
Furfural;
Furfuryl alcohol;
2-Mercapto propionic acid;
2-Methylfuran-3-thiol;
2-Methyldihydrofuran-3-thiol;
2-Methyltetrahydrofuran-3-thiol;
2-Ethylfuran-3-thiol;
2-Ethyldihydrofuran-3-thiol;
Methyl pyrazine;
2-Ethyl-3-methyl pyrazine;
Tetramethyl pyrazine;
Dipropyl disulfide;
Methyl benzyl disulfide;
Allyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;

n-Pentanal;
Hexanal;
Diacetyl;
Monosodium glutamate;
Sulfur-containing amino acids;
Cysteine;
Hydrolyzed vegetable protein;
Hydrolyzed fish protein; and
Tetramethyl pyrazine The 3-furyl alkyl disulfides, or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carragennan, other gums, and the like. The 3-furyl alkyl disulfides according to this invention can be incorporated with the carriers by conventional means such as spray-drying, drum-drying, and the like. Such carriers can also include materials for coacervating the 3-furyl alkyl disulfides (and other flavoring ingredients, as present) to provide encapsulated products. When the carrier is an emulsion the flavoring composition can also contain emulsifiers such as mono- and diglycerides of fatty acids and the like. With these carriers or vehicles, the desired physical form of the composition can be prepared.

The quantity of 3-furyl alkyl disulfides or mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate compositions contain from about 0.0005 parts per million (ppm) to about 250 ppm of 3-furyl alkyl disulfides. More particularly, in food compositions, it is desirable to use from about 0.0005 ppm to 100 ppm to enhancing flavors and in certain preferred embodiments of the invention, from about 0.2 to 50 ppm of the derivatives are included to add positive flavors to the finished product. All parts, proportions, percentages, and ratios herein are by weight unless otherwise indicated.

The amount of 3-furyl alkyl disulfides of our invention to be utilized in flavoring compositions can be varied over a wide range depending upon the particular quantity to be added to the foodstuff. Thus, amounts of one or more derivatives according to the present invention, of from about 2 ppm up to 80 or 90 percent of the total flavoring composition can be incorporated in such compositions. It is generally found to be desirable to include from about 10 ppm up to about 20 percent of the 3-furyl alkyl disulfide in such compositions.

The following examples are given to illustrate embodiments of the invention as it is preferably preferred to practice it. It will be understood that these examples are illustrative and the invention is not to be considered as restricted thereto except as indicated in the appended claims.

EXAMPLE I

PREPARATION OF METHYL(2,5-DIMETHYL-3-FURYL) DISULFIDE

Into a 25 ml Erlenmeyer flask equipped with magnetic stirrer, isopropyl alcohol-dry ice bath, thermometer and nitrogen tube is charged 0.942 g of dimethyl disulfide. The dimethyl disulfide is cooled to −30° C and 1.35 g of sulfuryl chloride is added dropwise with stirring under a nitrogen blanket. 8 cc of anhydrous diethyl ether and 2.12 g of sodium carbonate is then added to the reaction mass while maintaining the pot temperature at −20° to −25° C.

2.56 Grams of 2,5-dimethyl-3-furan thiol is then added dropwise over a 3-minute period to the reaction mass with stirring while maintaining the reaction mass at a temperature of −25° to −30° C.

After warming to 0° C, the reaction mass is then poured into 25 ml water and the resulting mixture is stirred. After separating, the organic phase is washed with one 10 ml portion of 5% sodium bicarbonate solution and one 10 ml portion of saturated sodium chloride solution. The organic phase is then dried and concentrated to yield an oil weighing 2.5 g. GLC analysis of the reaction mass confirms the presence of the following compounds:

| Peak A | 3.4% | $CH_3SSCH_3$ |
|---|---|---|
| Peak B | 20.8% | (2,5-dimethyl-3-furyl)-SH |
| Peak C | 35.6% | (2,5-dimethyl-3-furyl)-$S_2CH_3$ |
| Peak D | 39.7% | bis(2,5-dimethyl-3-furyl) disulfide |

(GLC Conditions: 25% SE-30, 8' × ¼" column)

Peak C, the desired product, is isolated by preparative GLC.

Mass spectral analysis, infrared analysis and NMR analysis confirm the structure as being:

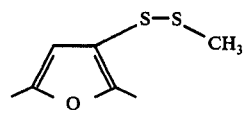

This material has a sweet, roasted meat aroma and sweet, roasted meat flavor with bloody and metallic nuances.

EXAMPLE II

PREPARATION OF ETHYL(2-METHYL-3-FURYL) DISULFIDE

Into a 25 ml Erlenmeyer flask equipped with magnetic stirrer, isopropyl alcohol dry ice bath, thermometer and nitrogen tube is placed 0.61 g of diethyl disulfide. The diethyl disulfide is cooled to −30° C and 0.675 g of sulfuryl chloride is added dropwise with stirring under a nitrogen blanket. 5 ml of anhydrous diethyl ether and 1.06 g of sodium carbonate is then added to the reaction mass while maintaining the pot temperature at −20° to −30° C.

2-Methyl-3-furan thiol (1.14 g) is added dropwise to the reaction mass with stirring while maintaining the reaction mass at a temperature of −25° to −30° C. After warming to −5° C, the reaction mass is then poured into 7 ml water and the resulting organic phase is separated and washed with one 10 ml portion of saturated sodium bicarbonate solution and one 10 ml portion of saturated sodium chloride solution. The organic phase is then dried and concentrated to yield an amber oil weighing 1.4 g. GLC analysis of the reaction mass confirms the presence of the following compounds:

| Peak A | 5.9% | (2-methyl-3-furanthiol structure) SH on furan |
| Peak B | 26.3% | $C_2H_5SSC_2H_5$ |
| Peak C | 23.2% | (ethyl 2-methyl-3-furyl disulfide structure) S—S—$C_2H_5$ |
| Peak D | 44.3% | (bis(2-methyl-3-furyl) disulfide structure) S—S |

Peak C, the desired product, is isolated by preparative GLC.

Mass spectral analysis, infrared analysis and NMR analysis confirm the structure as being:

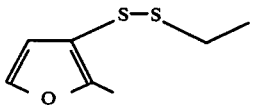

This material has a sweet, roasted, liver-like aroma and sweet, pot roast beef flavor with nutty, liver, bloody and metallic nuances.

EXAMPLE III

LARGE-SCALE PREPARATION OF ETHYL(2-METHYL-3-FURYL) DISULFIDE

Into a 250 ml three-neck flask equipped with magnetic stirrer, isopropyl alcohol dry ice bath, thermometer, Y-tube, drying tube, addition funnel and nitrogen inlet tube is placed 10.7 g of diethyl disulfide. The diethyl disulfide is cooled to −30° C and 11.8 g of sulfuryl chloride is added dropwise from the addition funnel with stirring under a nitrogen blanket over a period of 15 minutes. 70 ml of anhydrous diethyl ether (over a 15-minute period) and 18.5 g of sodium carbonate is then added to the reaction mass while maintaining the pot temperature at −30° to −35° C.

20 Grams of 2-methyl-3-furan thiol is then added dropwise over a 17-minute period to the reaction mass from the addition funnel with stirring while maintaining the reaction mass at a temperature of −25° to −30° C.

After warming to −15° C, the reaction mass is then poured into 120 ml water and the resulting mixture is stirred. Ether (20 ml) is added and the organic phase separated. The remaining aqueous phase is then extracted with 25 ml diethyl ether; the ether extracts are combined and washed with one 50 ml portion of saturated sodium bicarbonate solution and one 50 ml portion of saturated sodium chloride solution. The organic phase is then dried over anhydrous sodium sulfate, filtered and concentrated to yield a deep yellow oil weighing 28.1 g. GLC analysis of the reaction mass confirms the presence of the following compounds.

| Peak A | 1.0% | 2-Methyl-3-furanthiol |
| Peak B | 31.7% | Diethyl disulfide |
| Peak C | 20.5% | Ethyl(2-methyl-3-furyl) disulfide |
| Peak D | 44.5% | Bis(2-methyl-3-furyl) disulfide |

(GLC Conditions: 25% SE-30, 8' × ½" column)

Vacuum distillation of the crude product (28.1 g) yields the following fractions, each of which contain substantial quantities of product.

| Fraction No. | Wt. | Vapor Temperature | Pressure (mm Hg) | % Ethyl(2-methyl-3-furyl) disulfide |
|---|---|---|---|---|
| 2 | 0.8 g | 82–86° C | 5.6 | 95.1% |
| 3 | 1.87 g | 86–87° C | 5.7 | 95.4% |
| 4 | 1.80 g | 86–88° C | 5.4 | 95.6% |
| 5 | 0.76 g | 90–105° C | 5.7 | 89.8% |

This material has a sweet, roasted, liver-like aroma and sweet, pot roast beef flavor with nutty, liver, bloody and metallic nuances.

EXAMPLE IV

PREPARATION OF ETHYL(2,5-DIMETHYL-3-FURYL) DISULFIDE

Into a 25 ml Erlenmeyer flask equipped with magnetic stirrer, isopropyl alcohol dry ice bath, thermometer and nitrogen tube is placed 0.61 g of diethyl disulfide. The diethyl disulfide is cooled to −30° C and 0.675 g of sulfuryl chloride is added dropwise with stirring under a nitrogen blanket. 5 ml of anhydrous diethyl ether and 1.06 g of sodium carbonate is then added to the reaction mass while maintaining the pot temperature at −20° to −30° C.

1.28 Grams of 2,5-dimethyl-3-furan thiol is then added dropwise to the reaction mass with stirring while maintaining the reaction mass at a temperature of −20° to −30° C.

After warming to −5° C, the reaction mass is then poured into 13 ml water. 7 ml of diethyl ether are added and the resulting organic (diethyl ether) phase is separated and then washed with one 10 ml portion of saturated sodium bicarbonate solution and one 10 ml portion of saturated sodium chloride solution. The organic phase is then dried over anhydrous sodium sulfate and concentrated to yield an amber oil weighing 1.6 g. GLC analysis of the reaction mass confirms the presence of the following compounds:

| Peak A | 22.3% | C₂H₅SSC₂H₅ |
| Peak B | 6.0% | (2-methyl-3-furyl)-SH |
| Peak C | 29.5% | (2-methyl-3-furyl)-S-S-C₂H₅ |
| Peak D | 41.5% | bis(2-methyl-3-furyl) disulfide |

(GLC Conditions: 25% SE-30, 8' × ¼" column)

Peak C, the desired product, is isolated by preparative GLC.

Mass spectral analysis, infrared analysis and NMR analysis confirm the structure as being:

(2-methyl-3-furyl)-S-S-C₂H₅

This material has a sweet, roasted aroma and a sweet roasted coffee-like flavor.

EXAMPLE V

PREPARATION OF n-PROPYL(2-METHYL-3-FURYL) DISULFIDE

Into a 25 ml Erlenmeyer flask equipped with magnetic stirrer, isopropyl alcohol dry ice bath, thermometer and nitrogen tube is placed 0.75 g of di-n-propyl disulfide. The di-n-propyl disulfide is cooled to −30° C and 0.675 g of sulfuryl chloride is added dropwise with stirring under a nitrogen blanket. 5 ml of anhydrous diethyl ether and 1.06 g of sodium carbonate is then added to the reaction mass while maintaining the pot temperature at −20° to −30° C.

1.14 Grams of 2-methyl-3-furan thiol is then added dropwise to the reaction mass with stirring while maintaining the reaction mass at a temperature of −25° to −30° C.

After warming to 0° C, the reaction mass is then poured into 10 ml water. 5 ml diethyl ether are added and the resulting organic phase is then washed with one 10 ml portion of saturated sodium bicarbonate solution and one 10 ml portion of saturated sodium chloride solution. The organic phase is then dried and concentrated to yield a dark brown oil weighing 1.4 g. GLC analysis of the reaction mass confirms the presence of the following compounds:

| Peak A | 4.5% | (2-methyl-3-furyl)-SH |
| Peak B | 29.5% | 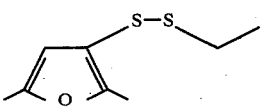 |
| Peak C | 36.6% | (2-methyl-3-furyl)-S-S-propyl |
| Peak D | 27.4% | bis(2-methyl-3-furyl) disulfide |

(GLC Conditions: 25% SE-30, 8' × ¼" column)

Peak C, the desired product, is isolated by preparative GLC.

Mass spectral analysis, infrared analysis and NMR analysis confirm the structure as being:

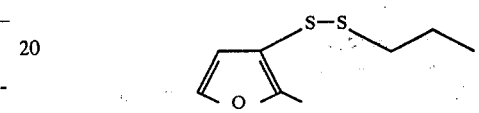

This material has a sweet, roasted meat, meaty aroma and a roast beef, roasted meat flavor with coffee, liver, bloody and metallic nuances.

EXAMPLE VI

LARGE SCALE PREPARATION OF n-PROPYL(2-METHYL-3-FURYL) DISULFIDE

Into a 250 ml three-neck flask equipped with magnetic stirrer, isopropyl alcohol dry ice bath, thermometer, Y-tube, addition funnel and nitrogen inlet tube is placed 13.1 g of di-n-propyl disulfide. The di-n-propyl disulfide is cooled to −32° C and 11.8 g of sulfuryl chloride is added dropwise from the addition funnel with stirring under a nitrogen blanket, over a period of 15 minutes. 70 ml of anhydrous diethyl ether and 18.5 g of sodium carbonate is then added to the reaction mass while maintaining the pot temperature at −30° to −35° C.

20 Grams of 2-methyl-3-furan thiol is then added dropwise to the reaction mass with stirring while maintaining the reaction mass at a temperature of −25° to −35° C.

After warming to −13° C, the reaction mass is then poured into 120 ml water and the resulting mixture is stirred. Ether (20 ml) is added and the organic phase separated. The remaining aqueous phase is extracted with 25 ml diethyl ether; the ether extracts are combined and washed with one 100 ml portion of saturated sodium bicarbonate solution and one 50 ml portion of saturated sodium chloride solution. The organic phase is then dried over anhydrous sodium sulfate, filtered and concentrated to yield a deep yellow oil weighing 30.6 g. GLC analysis of the reaction mass confirms the presence of the following compounds:

| Peak A | 34.5% | di-n-propyl disulfide |
| Peak B | 24.3% | n-propyl(2-methyl-3-furyl) disulfide |
| Peak C | 38.8% | bis(2-methyl-3-furyl) disulfide |

(GLC Conditions: 25% SE-30, 8' × ½" column)

Vacuum distillation of the crude product (30.6 g) yields the following fractions which contain substantial quantities of product:

| Fraction No. | Wt. | Vapor Temperature | Pressure (mm Hg) | % n-propyl (2-methyl-3-furyl) disulfide |
|---|---|---|---|---|
| 3 | .30 g | 97–97.5° C | 5.7 | 95.7% |
| 4 | 2.24 g | 97.5–98.5° C | 5.7 | 96.0% |
| 5 | 2.35 g | 98.5–99.5° C | 5.7 | 94.0% |
| 6 | 1.05 g | 99.5–102° C | 5.7 | 89.3% |
| 7 | 1.39 g | 100–107° C | 5.6 | 62.3% |

This material has a sweet, roasted meat, meaty aroma and a roast beef, roasted nut flavor with coffee, liver, bloody and metallic nuances.

EXAMPLE VII

PREPARATION OF n-PROPYL(2,5-DIMETHYL-3-FURYL) DISULFIDE

Into a 25 ml Erlenmeyer flask equipped with magnetic stirrer, isopropyl alcohol dry ice bath, thermometer and nitrogen tube is placed 0.75 g of di-n-propyl disulfide. The di-n-propyl disulfide is cooled to −30° C and 0.675 g of sulfuryl chloride is added dropwise with stirring under a nitrogen blanket. 5 ml of anhydrous diethyl ether and 1.06 g of sodium carbonate is then added to the reaction mass while maintaining the pot temperature at −25° to −30° C.

1.28 Grams of 2,5-dimethyl-3-furan thiol is then added dropwise to the reaction mass with stirring while maintaining the reaction mass at a temperature of −20° to −30° C.

After warming to 0° C, the reaction mass is then poured into 10 ml water. Diethyl ether is added and the resulting organic phase is then separated and washed with one 10 ml portion of saturated sodium bicarbonate solution and one 10 ml portion of saturated sodium chloride solution. The organic phase is then dried and concentrated to yield a dark brown oil weighing 1.7 g. GLC analysis of the reaction mass confirms the presence of the following compounds:

| Peak A | 3.2% | 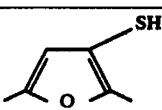 |
| --- | --- | --- |
| Peak B | 29.0% | 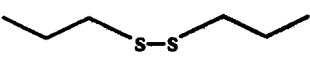 |
| Peak C | 29.0% | 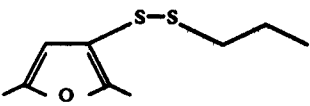 |
| Peak D | 36.1% | 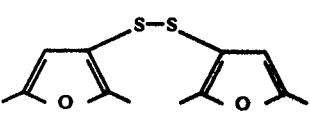 |

(GLC Conditions: 25% SE-30, 8' × ¼ " column)

Peak C, the desired product, is isolated by preparative GLC.

Mass spectral analysis, infrared analysis and NMR analysis confirm the structure as being:

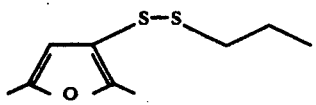

This material has a sweet, roasted, meat aroma with a hydrolyzed vegetable protein-like nuance and a roasted meat, sweet, hydrolyzed vegetable protein flavor with metallic and astringent nuances.

EXAMPLE VIII

PREPARATION OF ISOAMYL(2-METHYL-3-FURYL) DISULFIDE

Into a 25 ml Erlenmeyer flask equipped with magnetic stirrer, isopropyl alcohol dry ice bath, thermometer and nitrogen tube is placed 1.04 g of 3-methyl-1-butane thiol. The 3-methyl-1-butane thiol is cooled to −30° C and 1.35 g (0.8 ml) of sulfuryl chloride is added dropwise with stirring under a nitrogen blanket. 6 ml of anhydrous diethyl ether and 2.12 g of sodium carbonate are then added to the reaction mass while maintaining the pot temperature at −20° to −30° C.

1.14 Grams of 2-methyl-3-furan thiol is then added dropwise to the reaction mass with stirring while maintaining the reaction mass at a temperature of −20° to −30° C.

After warming to −5° C, the reaction mass is then poured into 13 ml water. 5 ml diethyl ether are added and the resulting organic phase is washed with one 10 ml portion of saturated sodium bicarbonate solution and one 10 ml portion of saturated sodium chloride solution. The organic phase is then dried and concentrated to yield a red-brown oil weighing 1.6 g. GLC analysis of the reaction mass confirms the presence of the following compounds:

| Peak A | 33.8% | 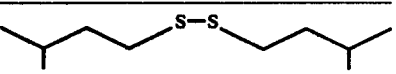 |
| --- | --- | --- |
| Peak B | 39.7% | 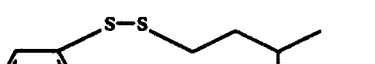 |
| Peak C | 23.1% |  |

(GLC Conditions: 25% SE-30, 8' × ¼ " column)

Peak B, the desired product, is isolated by preparative GLC.

Mass spectral analysis, infrared analysis and NMR analysis confirm the structure as being:

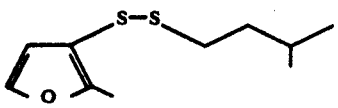

This material has a meaty-liver, chicken fat roasted aroma with metallic, rubbery, sweet and nutty nuances and a meaty, rubbery, roasted flavor with sweet and "baked goods" notes.

EXAMPLE IX

Reaction:

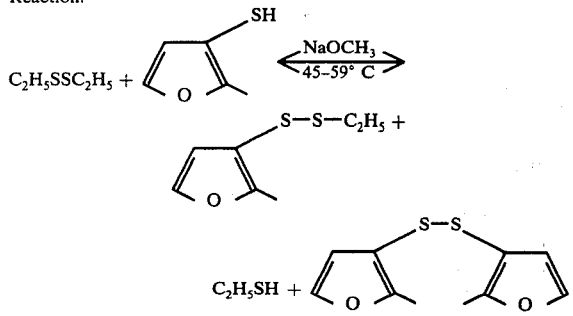

540 Grams (5.0 moles) of diethyl disulfide is added to a 1-liter three-necked reaction flask fitted with mechanical stirrer, pot thermometer, "Y" tube, 250 g addition funnel, dry ice-acetone trap and heating mantle. 1 Gram (0.0185 moles) of sodium methoxide is charged with stirring at room temperature (23° C). 114 Grams (1.0 mole) of 2-methyl-3-furanthiol is then added gradually over ten minutes, the reaction mass becoming a pale orange turbid solution, remaining at 23° C. The reaction mixture is then warmed to 50° C with stirring and maintained at 45°–59° C for a period of 14 hours and at 25° C for an additional 9 hours. Table II lists the GLC analysis of samples taken at various times to follow the progress of the reaction.

(GLC analysis is conducted on a F&M-700 chromatograph. Conditions used: 8 feet × ¼ inch column with 25% SE-30 on Chromsorb W, programmed 120° to 225° C at 5°/min. and helium flow rate of 80 ml/min. Samples are diluted with hexane, washed with 2% HCl and saturated NaCl solution, and dried with Na₂SO₄ before GLC analysis).

Table II

| Sample | Reaction Time (Hrs.) | Reaction Temp ° C. | GLC Ratio of | | |
|---|---|---|---|---|---|
| | | | Thiol Reactant | Ethyl(2-methyl-3-furyl)-disulfide | Difuryl Disulfide |
| A | 1 | 45–50 | 90.1 | 7.8 | 2.1 |
| B | 2 | 48–49 | 81.5 | 15.9 | 2.6 |
| C | 4 | 49–50 | 59.5 | 36.8 | 3.7 |
| D | 6.5 | 49–59 | 36.4 | 59 | 4.7 |
| E | {14, 9} | {51–52, 25} | 6.3 | 85.8 | 7.9 |

Hexane (350 ml) is added to the reaction mass with stirring followed by 50 ml of 2% aqueous HCl solution. The mixture is then transferred to a 2000 ml separatory funnel and additional hexane (150 ml) is added. After separating the aqueous layer (having a pH of between 1 and 2), the hexane layer is washed with two 50 ml portions of saturated sodium chloride solution; (the second wash liquor having a pH of between 4 and 5). The hexane solution is then dried over anhydrous sodium sulfate (50 g) and gravity filtered through filter paper. Hexane (50 ml) is used to rinse the sodium sulfate and the resulting rinse is then combined with the organic layer. The hexane solution is then charged to a 2-liter, 3-necked reaction flask fitted with a 2.8 × 30 cm. Vigreux column, variable reflux distilling head, capillary tube with nitrogen bleed and heating mantle.

The hexane is distilled (55°–72.5° C) at atmospheric pressure to a pot temperature of 124° C. A total of 321 g (89% hexane) is recovered. The unreacted diethyl disulfide is removed at 60°–64° C and 45–20 torr. to a pot temperature of 73° C., yielding 423 g of 97.3% diethyl disulfide, and 78 g of 90% hexane in the trap. After transfer to a 500 ml flask, the crude residue (150 g) is distilled under vacuum and the product collected in five fractions as listed in Table III. Fraction 5 being 98.6% product, having the structure:

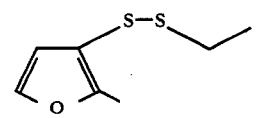

as confirmed by the following analyses:

Infra-Red: thin film, 2970, 2920, 2860, 1580, 1510, 1440, 1410, 1380, 1370, 1250, 1220, 1190, 1120, 1085, 935, 885, 755, 730, 645 and 595 cm$^{-1}$.

Nuclear Magnetic Resonance: CDCl$_3$, 1.31 (t, 3, J = 7.0 Hz), 2.35 (s, 3 CH$_3$), 2.72 (q, 2, J = 7.0 Hz), 6.40 (d, 1, J = 1.5 Hz), 7.24 ppm (d, 1, J = 1.5 Hz).

Mass Spectral Analysis: m/e (molecular ion, then decreasing intensity) 174, 113, 27, 43, 29, 45, 174, 69, 51.

This material has a sweet, roasted, liver-like aroma and sweet, pot roast, and roast beef flavor notes with nutty, liver, bloody and metallic nuances.

Table III

| Fraction No. | Wt. (g) | Vapor Temp. (° C.) | Pressure (mm Hg) | % Desired Product | % Thiol Reactant | % Diethyl Disulfide Reactant | % Difuryl Disulfide By-Product |
|---|---|---|---|---|---|---|---|
| 3 | 12.9 | 27–65 | 2.6 | 8.8 | — | 91.0 | — |
| 4 | 4.0 | 71–72.5 | 2.4 | 91.7 | — | 7.6 | 0.1 |
| 5 | 91.1 | 73–75 | 2.4 | 98.6 | — | 0.3 | 1.0 |
| 6 | 6.3 | 74–79 | 2.4 | 95.6 | 0.1 | 0.1 | 4.3 |
| 7 | 6.0 | 79–82 | 2.4 | 90.6 | 0.1 | 0.1 | 9.4 |
| Residue | 23.0 | — | — | 10.8 | 20.1 | 0.1 | 68.9 |

EXAMPLE X

Reaction:

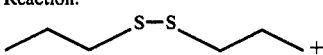 +

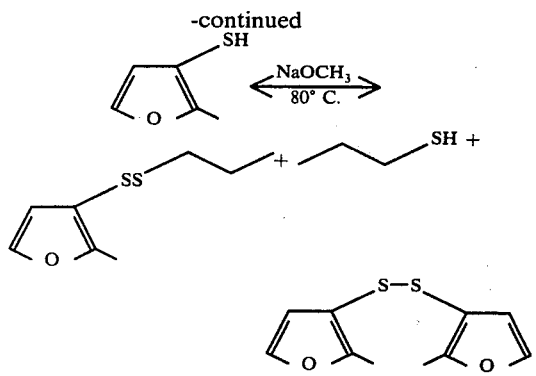

750 Grams (5.0 moles) of di-n-propyl disulfide is added to a 2-liter, three-necked reaction flask fitted with mechanical stirrer, pot thermometer, "Y" tube, 250 ml addition funnel, dry ice-acetone trap, and heating mantle. 1 Gram (0.0185 moles) of sodium methoxide is charged with stirring at room temperature (23° C). 114 Grams (1.0 moles) of 2-methyl-3-furanthiol is then added gradually over five minutes, the reaction mass becoming a pale orange turbid solution. The reaction mixture is then warmed to 80° C with stirring and maintained at 80° C for a period of 3.5 hours and at 25° C for an additional 16 hours. Table IV, infra, lists the GLC analysis of samples taken at various times to follow the progress of the reaction.

(GLC analysis is conducted on a F&M-700 chromatograph. Conditions used: 8 feet × ¼ inch column with 25% SE-30 on Chromsorb W, programmed 130° to 225° C at 5°/min. and helium flow rate of 80 ml/min. Samples are diluted with hexane, washed with 2% HCl and saturated NaCl solution, and dried with $Na_2SO_4$ before GLC analysis).

The hexane solution is dried over anhydrous sodium sulfate (50 g) and gravity filtered through filter paper. Hexane (100 ml) is used to rinse the sodium sulfate and is combined with the organic layer. The hexane solution is charged to a 2-liter, 3-necked reaction flask fitted with a 2.8 × 30 cm. Vigreux column, variable reflux distilling head, capillary tube with nitrogen bleed and heating mantle. The hexane is distilled (66°–72° C) at atmospheric pressure to a pot temperature of 124° C. A weight of 368 g (99% hexane) is recovered. The unreacted n-propyl disulfide is removed at 64°–68° C and 5.5–5.3 torr. to a pot temperature of 82° C, yielding 571 g of 95% n-propyl disulfide; 113 g of 99% hexane is in the trap. After transfer to a 500 ml flask, the crude residue (209.3 g) is distilled under vacuum and the product collected in six fractions as listed in Table V. Fractions 6 and 7 are the desired product having the structure:

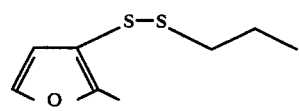

as confirmed by the following analyses:

Infra-Red, thin film, 2960, 2930, 2870, 1578, 1510, 1455, 1380, 1285, 1220, 1125, 1085, 935, 885, 730, 650 $cm^{-1}$.

Nuclear Magnetic Resonance: $CDCl_3$: 0.94 (t, 3, J = 7 Hz), 1.72 (m, 2, J = 7 Hz), 2.33 (s, 3, $CH_3$), 2.68 (t, 2, J = 7 Hz), 6.38 (d, 1, J = 1.5 Hz) and 7.22 (d, 1, J = 1.5 Hz) ppm.

Mass Spectral Analysis: m/e decreasing intensity: 82, 188 ($M^+$), 113, 114, 43, 41, 45, 39, 42, 112.

This material has a sweet, roasted meaty aroma and a roast beef, roasted nut flavor with coffee, liver, bloody and metallic nuances.

Table IV

| Sample | Reaction Time (Hrs.) | Reaction Temp. (° C.) | GLC Ratio | | |
|---|---|---|---|---|---|
| | | | Thiol Reactant | n-propyl (2-methyl-3-furyl)-disulfide | Difuryl Disulfide |
| A | 0.33 | 80–85 | 63.0 | 32.5 | 4.5 |
| B | 1.33 | 80–84 | 14.9 | 76.5 | 8.6 |
| C | 2.50 | 80–81 | 2.0 | 91.4 | 6.7 |
| D | 3.50 | 80 | 1.5 | 92.0 | 6.5 |
| E | { 3.50 / 16.00 } | { 80 / 25 } | 2.0 | 92.0 | 6.0 |

Hexane (600 ml) is added to the reaction mass with stirring followed by 50 g of 2% aqueous HCl solution. The mixture is then transferred to a 2-liter separatory funnel. After separating the aqueous layer (having a pH of between 1 and 2) the hexane layer is washed with two portions of 70 ml of saturated sodium chloride solution; the second wash liquor has a pH of between 4 and 5.

Table V

| Fraction No. | Wt. (g) | Vapor Temp. ° C. | Pressure mm. Hg. | % Desired Product | % Thiol Reactant | % Di-n-propyl Disulfide Reactant | % Difuryl Disulfide By-Product |
|---|---|---|---|---|---|---|---|
| 3 | 62.0 | 45–61 | 1.4 | 9.3 | — | 90.0 | — |
| 4 | 14.8 | 61–71 | 1.4 | 40.1 | — | 59.5 | 0.1 |
| 5 | 12.4 | 71–75.5 | 1.4 | 83.8 | — | 15.4 | 0.4 |
| 6 | 8.9 | 75.5–76 | 1.4 | 96.1 | — | 2.1 | 1.2 |
| 7 | 80.7 | 76–79 | 1.4 | 96.9 | — | 0.4 | 2.5 |
| 8 | 6.6 | 79–83 | 1.4 | 86.1 | — | 0.6 | 13.2 |
| Residue | 20.7 | — | — | 23.7 | 20.1 | 0.1 | 53.6 |

EXAMPLE XI

PREPARATION OF CYCLOHEXYL(2-METHYL-3-FURYL)-DISULFIDE

Reaction:

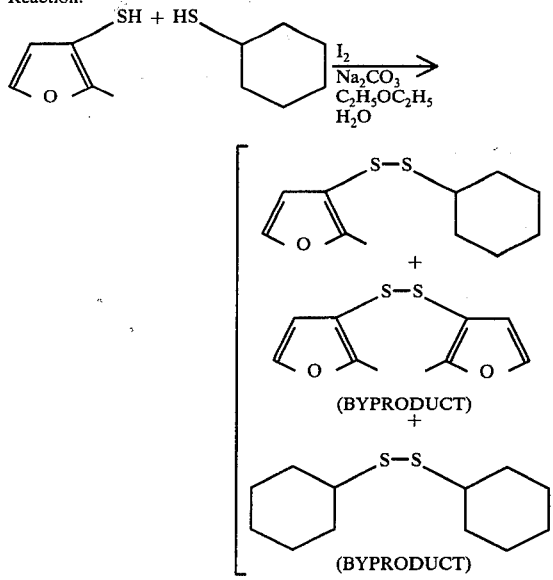

0.57 Grams (0.0050 moles) of 2-methyl-3-furanthiol and 1.16 grams (0.01 moles) of cyclohexylmercaptan are dissolved in 12 ml of diethyl ether. 0.8 Grams (0.0075 moles) of sodium carbonate dissolved in 8 ml water is added to the reaction mass. Over a period of 10 minutes, a solution of 1.9 grams (0.0075 moles) of iodine dissolved in 6 ml diethyl ether is added to the reaction mass with stirring until the iodine color remains. The reaction mass is then stirred over a period of 45 minutes.

The reaction mass is placed in a separatory funnel and the aqueous layer is separated from the organic layer. The organic layer is washed with 5 ml of saturated sodium bicarbonate solution followed by two 5 ml portions of 0.1 molar sodium thiosulfate. This material is then washed with one 10 ml portion of saturated chloride solution, and the organic layer is dried over anhydrous sodium sulfate and concentrated yielding 1.50 grams of a dark amber oil. The desired reaction product is isolated using gas-liquid chromatography apparatus (conditions: 8 feet × ¼ inch column, 25% SE-30) and is 99% pure. The structure is confirmed by mass spectral analysis, NMR analysis and IR analysis. Mass spectral analysis is as follows: m/e (decreasing intensity):

146, 55, 41, 113, 83, 228 (molecular ion), 82, 43, 45

This material has a meaty, liver and sweet aroma with a rubbery nuance and a sweet, liver, meaty flavor with rubbery and nutty nuances.

EXAMPLE XII

PREPARATION OF ISOAMYL (2,5-DIMETHYL-3-FURYL) DISULFIDE

Reaction:

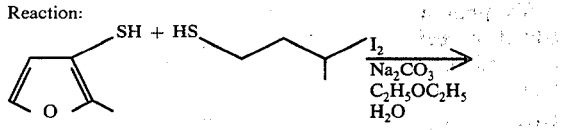

-continued

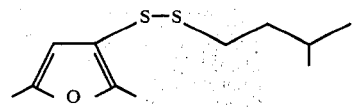

0.64 Grams (0.005 moles) of 2,5-dimethyl-3-furanthiol and 1.04 grams (0.01 moles) of isoamyl mercaptan are dissolved in 12 ml anhydrous diethyl ether. 0.8 Grams (0.0075 moles) of sodium carbonate dissolved in 8 ml water is added with stirring to the reaction mass. 1.9 Grams (0.0075 moles) of iodine dissolved in 6 ml anhydrous diethyl ether is then added dropwise to the reaction mass until the iodine color remains. The reaction mass is then stirred for a period of 30 minutes.

The reaction mass is then placed in a separatory funnel and the aqueous layer is separated from the organic layer. The organic layer is then washed with 5 ml saturated sodium bicarbonate, and one 4 ml portion of 0.1 molar sodium thiosulfate solution. The reaction mass is then filtered through anhydrous sodium sulfate and concentrated to yield a crude oil (1.32 grams dark brown oil).

The product is then isolated from the crude oil using gas-liquid chromatography apparatus (conditions: 8 feet × ¼ inch column, 25% SE-30). Mass spectral analysis, infrared analysis and NMR analysis yield the information that the isolated product has the structure:

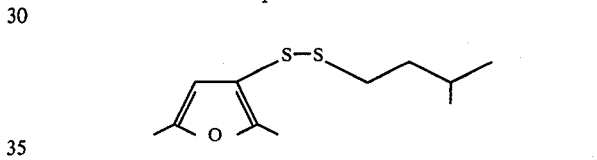

Mass spectral analysis: m/e (in decreasing intensity): 43, 230 (molecular ion), 127, 128, 96, 126, 160, 41, 71

This material has a sweet, floral, meaty, allium fragrance note and insofar as taste is concerned, it has a sulfury, rubbery, liver aroma and sweet, rubbery, sulfury flavor with skunky, liver and bitter nuances.

EXAMPLE XIII

The following ingredients are refluxed for four hours:

| Ingredient | Parts by Weight |
| --- | --- |
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for three days and an aliquot portion is withdrawn and dried. Based on the weight of the dry solid obtained, sufficient gum arabic is added to the batch to provide a composition containing one part by weight of gum arabic. The composition is then spray-dried.

Ethyl(2-methyl-3-furyl) disulfide is added to the spray-dried material at the rate of 4 ppm.

The resulting material has an excellent beef liver flavor.

EXAMPLE XIV

A beef liver gravy is made by formulating a composition in the amounts indicated:

| Ingredient | Parts by Weight |
| --- | --- |
| Cornstarch | 10.50 |
| The final product of Example XIII | 3.00 |
| Caramel color | .30 |
| Garlic powder | .05 |
| White pepper | .05 |
| Salt | 1.90 |
| Monosodium glutamate | .20 |

To one unit of gravy flavor concentrate, eight ounces of water is added and the mixture is stirred thoroughly to disperse the ingredients brought to a boil, simmered for one minute, and served. This "meatless" gravy exhibits an excellent beef-liver flavor.

EXAMPLE XV

USE OF ETHYL(2-METHYL-3-FURYL) DISULFIDE

Seven ppm ethyl(2-methyl-3-furyl) disulfide is added to beef broth prepared from a commercial dried mixture and 250 ml hot water. The ethyl(2-methyl-3-furyl) disulfide increases the beef-liver character and imparts a pleasant nutty note. The resultant beef broth has an improved more blended meaty flavor than does the unflavored beef broth.

EXAMPLE XVI

The following ground sausage mixture is prepared:

| Ingredient | Parts by Weight |
| --- | --- |
| Ground beef | 200 |
| Beef suet | 120 |
| Ice/NaCl (50:50 mixture) | 200 |
| Potato flour | 100 |
| Anhydrous bread crumbs | 140 |
| Dry milk powder | 20 |
| Standard spice flavor containing: | 10 |
| Oil of cumin | 1.6 |
| Oil of mustard | 3.3 |
| Oil of celery | 3.3 |
| Oil of ginger | 5.2 |
| Oil of cloves | 14.3 |
| Oil of coriander | 17.6 |
| Oil of pimenta berries | 22.0 |
| Oil of black pepper | 43.0 |
| Oleoresin capsicum | 373.0 |
| Oil of nutmeg | 500.0 |

To the above mixture 0.02% by weight of the following mixture is added:

| Ingredient | Parts by Weight |
| --- | --- |
| n-Propyl(2-methyl-3-furyl) disulfide prepared according to Example X, Example V or Example VI | 5 |
| Ethyl alcohol (95%) | 95 |

The resulting mixture is then formed into a sausage and encased in the usual manner. The encased sausage is heated in water at a temperature of 160°-180° F for a period of two hours. This sausage has a liver-taste reminiscent of the taste of sausage made with natural liver.

EXAMPLE XVII

A mixture of 8.8 g of cysteine-hydrochloride, 8.8 g of thiamine hydrochloride and 309.4 of carbohydrate-free vegetable protein hydrolysate is brought to a standard weight of 1000 grams by the addition of water and adjusted to 4.75 pH with acid or base as required. This mixture is then boiled under reflux conditions at atmospheric pressure for four hours and allowed to cool.

After the mixture is allowed to cool, one gram of isoamyl(2-methyl-3-furyl) disulfide prepared according to Example VIII is added thereto. The resulting mixture thus obtained has an excellent unique roasted, livery, meaty flavor with chicken meat nuances.

EXAMPLE XVIII

The following ground sausage mixture is prepared:

| Ingredient | Parts by Weight |
| --- | --- |
| Ground beef | 200 |
| Beef suet | 120 |
| Ice/NaCl (50:50 mixture) | 200 |
| Potato flour | 100 |
| Anhydrous bread crumbs | 140 |
| Dry milk powder | 20 |
| Standard spice flavor containing: | 10 |
| Oil of cumin | 1.6 |
| Oil of mustard | 3.3 |
| Oil of celery | 3.3 |
| Oil of ginger | 5.2 |
| Oil of cloves | 14.3 |
| Oil of coriander | 17.6 |
| Oil of pimenta berries | 22.0 |
| Oil of black pepper | 43.0 |
| Oleoresin capsicum | 373.0 |
| Oil of nutmeg | 500.0 |

To the above mixture, 0.02% by weight of the following mixture is added:

| Ingredient | Parts by Weight |
| --- | --- |
| Methyl(2,5-dimethyl-3-furyl) disulfide (prepared according to Example I) | 4 |
| Ethyl(2,5-dimethyl-3-furyl) disulfide (prepared according to Example IV) | 4 |
| Ethyl alcohol (95%) | 95 |

The resulting mixture is then formed into a sausage and encased in the usual manner. The encased sausage is heated in water at a temperature of 160°-180° F for a period of two hours. This sausage has a unique pleasant sweet meat taste.

EXAMPLE XIX

A mixture of 8.8 g of cysteine-hydrochloride, 8.8 g of thiamine hydrochloride and 309.4 of carbohydrate-free vegetable protein hydrolysate is brought to a standard weight of 1000 grams by the addition of water, and adjusted to 4.75 pH with acid or base as required. This mixture is then boiled under reflux conditions at atmospheric pressure for four hours and allowed to cool.

After the mixture is allowed to cool, one gram of n-propyl(2,5-dimethyl-3-furyl) disulfide of Example VII is added thereto. The resulting mixture thus obtained has an excellent sweet, roasted meat flavor with pleasant vegetable notes.

EXAMPLE XX

USE OF n-PROPYL(2,5-DIMETHYL-3-FURYL) DISULFIDE

Six ppm n-propyl(2,5-dimethyl-3-furyl) disulfide is added to beef broth from a commercial dried mixture and 250 ml hot water. The n-propyl(2,5-dimethyl-3-furyl) difulfide increases the sweet meaty and vegetable character. The resultant beef broth has an improved more blended meaty flavor than does the unflavored beef broth.

EXAMPLE XXI

The following ingredients are refluxed for four hours:

| Ingredient | Parts by Weight |
| --- | --- |
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for three days and an aliquot portion is withdrawn and dried. Based on the weight of the dry solid obtained, sufficient gum arabic is added to the batch to provide a composition containing one part by weight of gum arabic. The composition is then spray-dried.

Cyclohexyl(2-methyl-3-furyl) disulfide is added to the spray-dried material at the rate of 8 ppm.

The resulting material has an excellent beef liver flavor.

EXAMPLE XXII

A beef liver gravy is made by formulating a composition in the amounts indicated:

| Ingredient | Parts by Weight |
| --- | --- |
| Cornstarch | 10.50 |
| The final product produced according to the process of Example XXI | 3.00 |
| Caramel color | .30 |
| Garlic powder | .05 |
| White pepper | .05 |
| Salt | 1.92 |
| Monosodium glutamate | .20 |

To one unit of gravy flavor concentrate, eight ounces of water is added, and the mixture is stirred thoroughly to disperse the ingredients brought to a boil, simmered for one minute, and served. This "meatless" gravy exhibits an excellent beef-liver flavor.

EXAMPLE XXIII

USE OF CYCLOHEXYL(2-METHYL-3-FURYL) DISULFIDE

Ten ppm cyclohexyl(2-methyl-3-furyl) disulfide is added to beef broth prepared from a commercial dried mixture and 250 ml hot water. The cyclohexyl (2-methyl-3-furyl) disulfide increases the sweet meaty and liver-like character and imparts a pleasant nutty note. The resultant beef broth has an improved more blended meaty flavor than does the unflavored beef broth.

EXAMPLE XXIV

The following ingredients are refluxed for four hours:

| Ingredient | Parts by Weight |
| --- | --- |
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for three days and an aliquot portion is withdrawn and dried. Based on the weight of the dry solid obtained, sufficient gum arabic is added to the batch to provide a composition containing one part by weight of gum arabic. The composition is then spray-dried.

Isoamyl(2,5-dimethyl-3-furyl) disulfide is added to the spray-dried material at the rate of 7 ppm.

The resulting material has an excellent beef liver flavor.

EXAMPLE XXV

A beef liver gravy is made by formulating a composition in the amounts indicated:

| Ingredient | Parts by Weight |
| --- | --- |
| Cornstarch | 10.50 |
| The final product produced according to the process of Example XXIV | 3.00 |
| Caramel color | .30 |
| Garlic powder | .05 |
| White pepper | .05 |
| Salt | 1.92 |
| Monosodium glutamate | .20 |

To one unit of gravy flavor concentrate, eight ounces of water is added and the mixture is stirred thoroughly to disperse the ingredients brought to a full boil, simmered for one minute and served. This "meatless" gravy exhibits an excellent beef-liver flavor.

EXAMPLE XXVI

USE OF ISOAMYL(2,5-DIMETHYL-3-FURYL) DISULFIDE

Six ppm isoamyl(2,5-dimethyl-3-furyl) disulfide is added to beef broth prepared from a commercial dried mixture and 250 ml hot water. The isoamyl (2,5-dimethyl-3-furyl) disulfide imparts a liver and sweet meaty character. The resultant beef broth has an improved more blended meaty flavor than does the unflavored beef broth.

EXAMPLE XXVII

PREPARATION OF n-HEPTYL(2-METHYL-3-FURYL) DISULFIDE

Reaction:

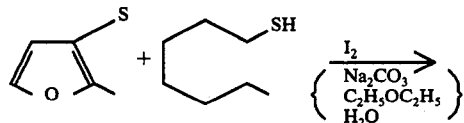

-continued

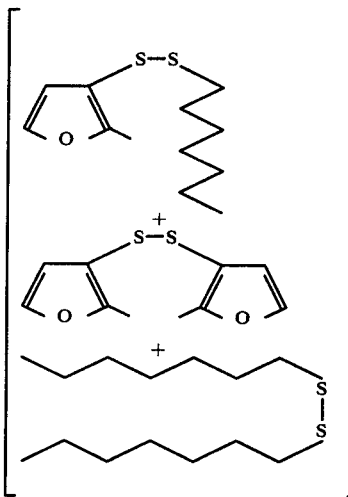

0.57 Grams (0.0050 moles) of 2-methyl-3-furanthiol and 1.32 grams (0.01 moles) of n-heptylmercaptan are dissolved in 12 ml of diethyl ether. 0.8 Grams (0.0075 moles) of sodium carbonate dissolved in 8 ml water is added to the reaction mass. Over a period of 20 minutes, a solution of 1.9 grams (0.0075 moles) of iodine dissolved in 6 ml diethyl ether is added to the reaction mass with stirring until the iodine color remains. The reaction mass is then stirred over a period of 35 minutes.

The reaction mass is placed in a separatory funnel and the aqueous layer is separated from the organic layer. The organic layer is washed with 5 ml of saturated sodium bicarbonate solution followed by two 5 ml portions of 0.1 molar sodium thiosulfate. This material is then washed with one 5 ml portion of saturated chloride solution, and the organic layer is dried over anhydrous sodium sulfate and concentrated yielding 1.44 grams of an amber oil. The desired reaction product is isolated using gas-liquid chromatography apparatus (conditions: 8 feet × ¼ inch column, 25% SE-30) and is 96.5% pure containing the following materials:

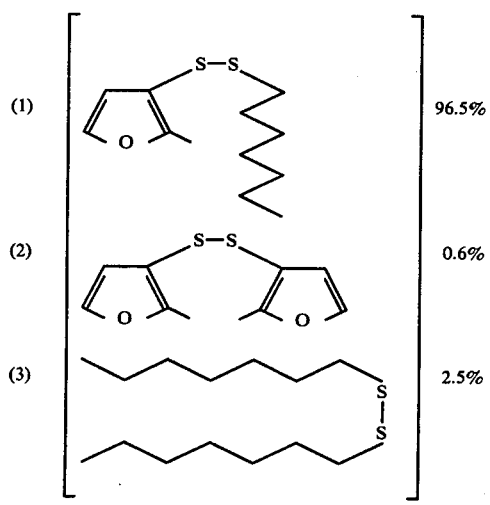

The structure is confirmed by mass spectral analysis, NMR analysis and IR analysis. Mass spectral analysis is as follows: m/e (decreasing intensity): 244($M^{30}$); 57, 113, 146, 43, 41, 82, 45, 55, 114

This material has a sulfury, roasted and meaty aroma with a roast beefy nuance and a sulfury, roasted and meaty flavor with a roast beefy nuance.

EXAMPLE XXVIII

The following ingredients are refluxed for four hours:

| Ingredient | Parts by Weight |
|---|---|
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for three days and an aliquot portion is withdrawn and dried. Based on the weight of the dry solid obtained, sufficient gum arabic is added to the batch to provide a composition containing one part by weight of gum arabic. The composition is then spray-dried.

n-Heptyl(2-methyl-3-furyl) disulfide is added to the spray-dried material at the rate of 4 ppm.

The resulting material has an excellent roast beef flavor.

EXAMPLE XXIX

A roast beef gravy is made by formulating a composition in the amounts indicated:

| Ingredient | Parts by Weight |
|---|---|
| Cornstarch | 10.50 |
| The final product of Example XXVIII | 3.00 |
| Caramel color | .30 |
| Garlic powder | .05 |
| White pepper | .05 |
| Salt | 1.92 |
| Monosodium glutamate | .20 |

To one unit of gravy flavor concentrate, eight ounces of water is added and the mixture is stirred thoroughly to disperse the ingredients brought to a boil, simmered for one minute, and served. This "meatless" gravy exhibits an excellent roast beef flavor.

What is claimed is:

1. A process for altering, or enhancing the liver flavor of a foodstuff comprising the step of adding to said foodstuff a liver flavor altering, modifying or enhancing quantity of a 3-furan-alkyl disulfide selected from the group consisting of:
Ethyl(2-methyl-3-furyl) disulfide;
Isoamyl(2-methyl-3-furyl) disulfide;
Cyclohexyl(2-methyl-3-furyl) disulfide; and
Isoamyl(2,5-dimethyl-3-furyl) disulfide.

2. A liver flavor altering modifying or enhancing composition comprising (i) a 3-furyl alkyl-disulfide compound selected from the group consisting of:
Ethyl(2-methyl-3-furyl) disulfide;
Isoamyl(2-methyl-3-furyl) disulfide;
Cyclohexyl(2-methyl-3-furyl) disulfide; and
Isoamyl(2,5-dimethyl-3-furyl) disulfide.
and (ii) a flavoring adjuvant for said 3-furylalkyl disulfide compound selected from the group consisting of:
4-methyl-5-beta-hydroxyethyl thiazole;
2-Methyl butanethiol;
4-Mercapto-2-butanone;

3-Mercapto-4-pentanone;
1-Mercapto-2-propanone;
Benzaldehyde;
Furfural;
Furfuryl alcohol;
2-Mercapto propionic acid;
2-Methylfuran-3-thiol;
2-Methyldihydrofuran-3-thiol;
2-Methyltetrahydrofuran-3-thiol;
2-Ethylfuran-3-thiol;
2-Ethyldihydrofuran-3-thiol;
Methyl pyrazine;
2-Ethyl-3-methyl pyrazine;
Tetramethyl pyrazine;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
Hydrolyzed fish protein; and
Tetramethyl pyrazine.

* * * * *